United States Patent [19]
Dancs et al.

[11] Patent Number: 5,547,616
[45] Date of Patent: Aug. 20, 1996

[54] DEVICE FOR DISPENSING A VOLATILE ACTIVE INGREDIENT

[75] Inventors: Imre J. Dancs, Greendale; Frank Savage, Germantown, both of Wis.

[73] Assignee: S. C. Johnson & Son, Inc., Racine, Wis.

[21] Appl. No.: 437,002

[22] Filed: May 8, 1995

[51] Int. Cl.⁶ ............................................. B01F 3/04
[52] U.S. Cl. .............................. 261/26; 261/30; 261/100; 261/DIG. 65; 422/124
[58] Field of Search ..................... 261/DIG. 65, 30, 261/26, 100; 422/124

[56] References Cited

U.S. PATENT DOCUMENTS

| | | |
|---|---|---|
| 3,990,848 | 11/1976 | Corris . |
| 4,035,451 | 7/1977 | Tringali . |
| 4,059,422 | 11/1977 | Steiner .............................. 261/DIG. 65 |
| 4,208,012 | 6/1980 | Dutcher ........................... 261/DIG. 65 |
| 4,276,236 | 6/1981 | Sullivan et al. . |
| 4,294,778 | 10/1981 | DeLuca ................................... 422/124 |
| 4,301,095 | 11/1981 | Mettler et al. . |
| 4,370,300 | 1/1983 | Mori et al. ........................ 261/DIG. 65 |
| 4,377,399 | 3/1983 | Bryson . |
| 4,432,938 | 2/1984 | Meetze, Jr. . |
| 4,666,638 | 5/1987 | Baker et al. . |
| 4,695,434 | 9/1987 | Spector . |
| 4,743,406 | 5/1988 | Steiner et al. . |
| 4,830,791 | 5/1989 | Muderlak et al. . |
| 4,840,770 | 6/1989 | Walz et al. . |
| 4,857,240 | 8/1989 | Kearnes et al. ............................ 261/26 |
| 4,931,224 | 6/1990 | Holzner, Sr. . |
| 5,133,042 | 7/1992 | Pelonis . |
| 5,147,582 | 9/1992 | Holzner, Sr. et al. . |
| 5,168,654 | 12/1992 | Chien . |
| 5,175,791 | 12/1992 | Muderlak et al. . |
| 5,250,232 | 10/1993 | Pepper et al. . |
| 5,259,062 | 11/1993 | Pelonis . |
| 5,282,334 | 1/1994 | Kimura et al. . |
| 5,370,829 | 12/1994 | Kunze . |
| 5,376,338 | 12/1994 | Zlotnik . |

Primary Examiner—Tim R. Miles

[57] ABSTRACT

A dispensing device for dispensing a volatile active ingredient from an air-transmitting substrate that forms a part of a refill assembly. The dispensing device includes a housing with an intake vent and an exit vent and an air flow path extending between them. Refill assembly support means are provided for removably supporting the refill assembly with its substrate located in the air flow path. Battery-powered fan means are provided for propelling air from the intake vent through the substrate and out the exit vent. A battery holder holds a fan battery in such a manner that a refill assembly not fully inserted within the refill assembly support means blocks the placement of a battery in the battery holder, while a battery correctly held in the battery holder blocks the removal from the air flow path of a refill assembly supported by the refill assembly support means. Thus, successful placement of a battery in the battery holder serves to both verify and maintain the correct placement of the refill assembly in the air flow path. An air-transmitting refill assembly for use with the dispensing device includes an air-transmitting substrate and a tab attached to the margin of the substrate. The tab has a brace surface facing generally away from the substrate and shaped to engage the surface of a battery being held within the battery holder of the dispensing device.

22 Claims, 6 Drawing Sheets

DEVICE FOR DISPENSING A VOLATILE ACTIVE INGREDIENT

TECHNICAL FIELD

The present invention relates generally to devices for dispensing volatile active ingredients. More particularly, the invention relates to such devices wherein the volatile active ingredient is applied to an air-transmitting substrate that is held within an airflow path within the device.

BACKGROUND ART

The art has produced a variety of fan-driven devices for dispensing volatile materials into the air. Typically such devices include a housing, an air inlet and outlet with an airflow path extending therebetween, a fan to produce an airflow in the airflow path, and a variety of means for introducing the volatile materials into the airflow path. A number of these fan-driven devices utilize battery power to drive the fan.

Of particular relevance to the instant invention are such devices that utilize a replaceable cartridge or refill assembly for renewing the supply of volatile materials to be dispensed by the device. The potential always exists for incorrect placement of the refill assembly or the battery when either is changed.

The art has addressed this difficulty in various ways. For example, Corris, U.S. Pat. No. 3,990,848, utilizes a box-like container with holes in its sides. The container contains a solid, cylindrical block of a volatilizable gel. A thin, rectangular battery is mounted on top of the container, with the battery's terminals placed so as to engage electrical contacts that lead to the fan of the device. The entire cartridge, with attached gel and affixed battery, is inserted as a unit into the housing of the device so that correct placement of the container automatically provides for correct placement of the battery.

Sullivan et al., U.S. Pat. No. 4,276,236 and Tringali, U.S. Pat. No. 4,035,451, both disclose a cylindrical cartridge having a conventional, cylindrical battery held at the longitudinal axis of the cartridge, with a space between the battery and the outer wall of the cartridge holding a fluted strip of paper bearing active ingredient. The battery is integrally fastened within the cartridge.

Steiner et al., U.S. Pat. No. 4,743,406, shows an arrangement somewhat similar to Sullivan et al. and Tringali, except that the cylindrical battery is not fastened within the cartridge. Instead, the battery simply removably slips into a battery chamber designed to hold the battery with its longitudinal axis vertical. The battery chamber is open at the center of its floor so that, once a battery is placed within the chamber and the cartridge is inserted into the Steiner et al. device, spring clip terminals can engage both ends of the battery, to lead power to the fan.

Walz et al., U.S. Pat. No. 4,840,770, show a generally cylindrical cartridge that has a shallow well occupying its uppermost portion. The well is filled with a gel-like odor control product. A cylindrical battery is clipped into a slot formed in the underside of the cartridge, with the longitudinal axis of the battery oriented at right angles to the longitudinal axis of the cylindrical cartridge. Airflow impinges the cartridge only from above and does not pass through the length of the cartridge.

Holzner, Sr., U.S. Pat. No. 4,931,224, and Holzner, Sr. et al., U.S. Pat No. 5,147,582, show a generally cylinder cartridge that is reminiscent of Sullivan et al., at least in the fact that volatile material is held in an annular space that surrounds and is co-axial with a cylindrical battery. However, in the two Holzner patents, the battery is removably held within a central well, so that the battery may be removed and replaced without the need to discard the entire cartridge. In essence, the cartridge is a holder for the battery, requiring that the cartridge be in place to hold the battery within the device.

Zlotnik, U.S. Pat. No. 5,376,338, employs a ring made of a block of vaporizable material that has air passages formed within it. This ring of material is held by a sleeve that, in turn, rests upon one end of a conventional, cylindrical battery. The longitudinal axis of the battery is vertical and located within the airflow of the device. The body of the battery thus serves as a supporting structure to hold up the sleeve that in turn holds up the ring of volatilizable material. The battery can be placed in the device without the block of vaporizable material, but the cartridge cannot be held within the device without the battery.

All of these devices in which a refill cartridge of some sort is associated with a battery either are designed to provide a compact or convenient arrangement or, in some instances, to require that a battery be changed when the rest of the cartridge is changed, renewing simultaneously both the electrical source and the source of volatile material to be dispensed by the device. However, none of this art presents an arrangement in which an air transmitting substrate bearing a volatile active ingredient is held by a refill assembly that is used in association with but remains separate from the battery such that successful placement of the battery within the device requires that the refill assembly have been correctly installed so that the substrate is held within an airflow through the device, with the further advantage of placement of the battery in a non-obstructing position with respect to the airflow.

An important problem for a user of a battery-powered, fan-driven device to dispense a volatile material is detecting or predicting when either the battery or the volatile material is or will be depleted. This especially can be important when the volatile is an insect control agent used in a sleeping room, for example, so that a dead battery or depleted volatile may mean an irritating midnight mosquito attack, with the attendant risk of mosquito-borne disease, in some locales.

The art is aware of the use in these devices of various control mechanisms that provide use-up indicators or timing circuits to measure the use or indicate the depletion of either the battery or the volatile material being dispensed. For example, Muderlak et al., U.S. Pat. No. 4,830,791, shows a timing circuit that provides a visual indication that a set number of days have passed since operation of the device was initiated or a reset switch was last pressed. The volatile material used in Muderlak lasts about 30 days, so the device is set to give a visual indication of the passage of time at 32 days. The timer operates by generating electrical pulses at set time intervals. A counter generates a latch signal when it has received a predetermined number of pulses.

Walz et al. does not include a timer or indicator device but does utilize an amount of a gel-like odor control product selected to be sufficient that battery life and the life of the volatile ingredient are about the same. As a consequence, the "product and battery can be installed and replaced at the same time as a unit, thus assuring that an old battery is not left in by mistake." (Column 7 at Lines 49–52).

The Tringali cartridge, also shown in Sullivan et al., permanently mounts the battery within the same cartridge that carries the device's supply of volatile ingredient.

Although no use-up indicator is supplied, at least the battery and volatile material must of necessity be replaced at the same time.

Muderlak et al., U.S. Pat. No. 5,175,791 uses a timer circuit to step up power over time to the heater utilized to cause the active ingredient to be dispensed. The Muderlak et al. '791 device is not battery driven, does not utilize a fan, and is noted only for its general use of a timer circuit.

Kunze, U.S. Pat. No. 5,370,829, discloses timed operation of the battery-driven fan of the device. However, the timer appears not to be designed to measure consumption of either battery power or volatile ingredient.

To be flexible in use, it is valuable that a device of the sort being discussed be capable of assuming more than one orientation, to allow the airflow coming from the device to be directed toward a desired part of the airspace of a room, for example, from different locations about the room. The presence of a heavy battery within the housing of an otherwise light-weight device can present some difficulties in accomplishing this.

A few of the devices shown in the art provide for more than one orientation of the device. Thus, the device shown in Baker et al., U.S. Pat. No. 4,666,638 is designed to either be wall mounted or supported by a flat surface. An anti-roll chamfered segment is formed in the housing of the Baker et al. device to allow it to sit stably on a flat surface, with the air discharged from the device angled upwardly. When the same device is mounted on a wall, it is securely fastened to the wall with the airflow directed horizontally, outwardly from the wall.

The device shown in Chien, U.S. Pat. No. 5,168,654, utilizes a clip leg to achieve two different orientations on a flat surface. In the first orientation, the clip leg is folded flat against the housing of the device, and the airflow is projected directly upwardly from the device. In the second position, the clip leg is opened to brace the device upwardly from the flat surface at an angle. The Chien device utilizes a heater to dispense an active ingredient from a solid repellent and is not battery operated.

Various other devices exist in the art, and those referred to, above, are by way of example only. The art is still in need of a device that provides an easy means for a user to detect when a replaceable substrate bearing an active ingredient has been improperly inserted into the device. Similarly, the art still is need of an elegant design that allows a user to control the direction of airflow from a battery powered blower device, as well as such a device that signals the user when battery power is about to or has become insufficient for effective use of the device. All of these features are important to a practical and useful battery operated device for dispensing a volatile active ingredient into the air.

BRIEF SUMMARY OF THE INVENTION

The dispensing device of the invention is designed to dispense a volatile active ingredient from an air-transmitting substrate that forms a part of a refill assembly. The dispensing device is summarized in that it includes a housing having an intake vent and an exit vent. Internal surfaces of the housing define an air flow path extending between the intake and exit vents. The dispensing device includes refill assembly support means for removably supporting the refill assembly with the substrate located in the air flow path. The dispensing device also includes battery-powered fan means for propelling air entering the housing by way of the intake vent along the air flow path, to pass through the substrate and exit by way of the exit vent.

A battery holder is also included for holding a battery for powering the fan means. The battery holder holds the battery in such a manner that a refill assembly not fully inserted within the refill assembly support means blocks the placement of a battery in the battery holder. Furthermore, the presence of a battery correctly held in the battery holder blocks the removal from the air flow path of a refill assembly supported in the air flow path by the refill assembly support means. As a consequence, successful placement of a battery in the battery holder serves to both verify and to maintain the correct placement of the refill assembly in the air flow path.

The dispensing device of the invention may alternatively be summarized in that it has a housing that includes a housing face forming the front of the housing, together with a housing roof, sides, and floor. The housing floor includes a foot upon which the housing may rest when placed on a supporting, generally flat surface. The housing floor also includes an angled support surface extending upwardly to the face from the forward margin of the foot at an acute angle to the foot. The housing has an intake vent and an exit vent, internal surfaces of the housing defining an air flow path extending between the intake and exit vents. The exit vent is located in the housing roof to vent the air flow upwardly when the housing is resting on the foot. The dispensing device of the invention also includes refill assembly support means for supporting the refill assembly with the substrate in the air flow path. Battery-powered fan means propels air entering the housing by way of the intake vent along the air flow path, to pass through the substrate and exit by way of the exit vent.

The dispensing device further includes a battery holder for holding a battery to power the fan means, with the battery positioned sufficiently far forward that the weight of the battery so interacts with the weights of the components of the dispensing device that the center of gravity of the dispensing device is above the foot, when the foot is resting on a horizontal surface, and is above the angled support surface, when the angled support surface is resting on a horizontal surface. By this means, the dispensing device may be supported alternatively and with positional stability by either the foot or the angled support surface to direct the air flow exiting the exit vent either upwardly or upwardly at a forward angle.

The air-transmitting refill assembly of the invention is summarized as follows. The refill assembly has a front and a rear and includes an air-transmitting substrate. A tab is attached to the rearward margin of the substrate. The tab has a brace surface facing generally away from the substrate. The brace surface is shaped to engage the surface of a battery being held within the battery holder of the dispensing device.

DETAILED DESCRIPTION OF THE PREFERRED EMBODIMENT

Figure 1:
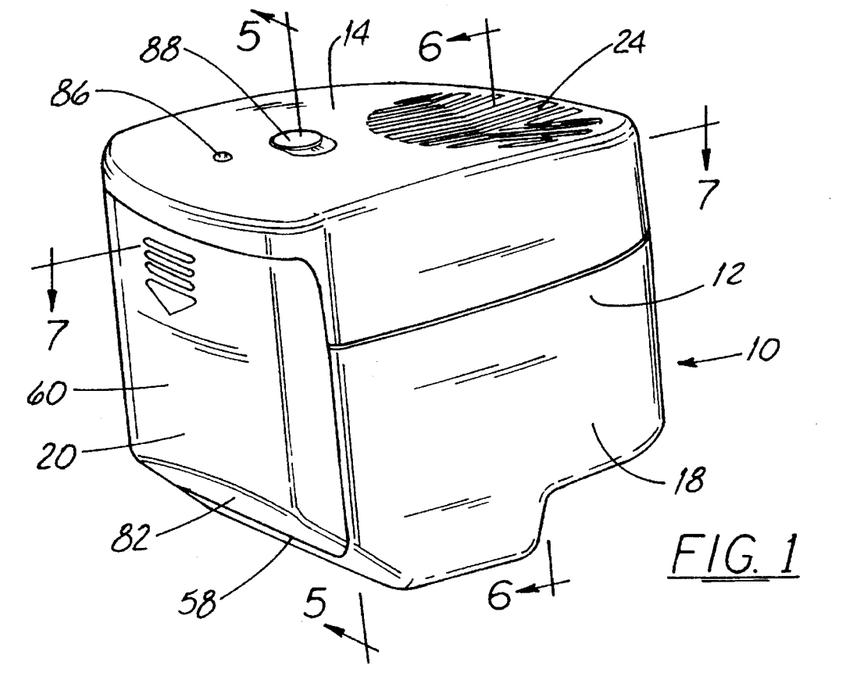
FIG. 1 is a front perspective view from above of a preferred embodiment of the dispensing device of the invention for dispensing a volatile active ingredient.
Figure 2:
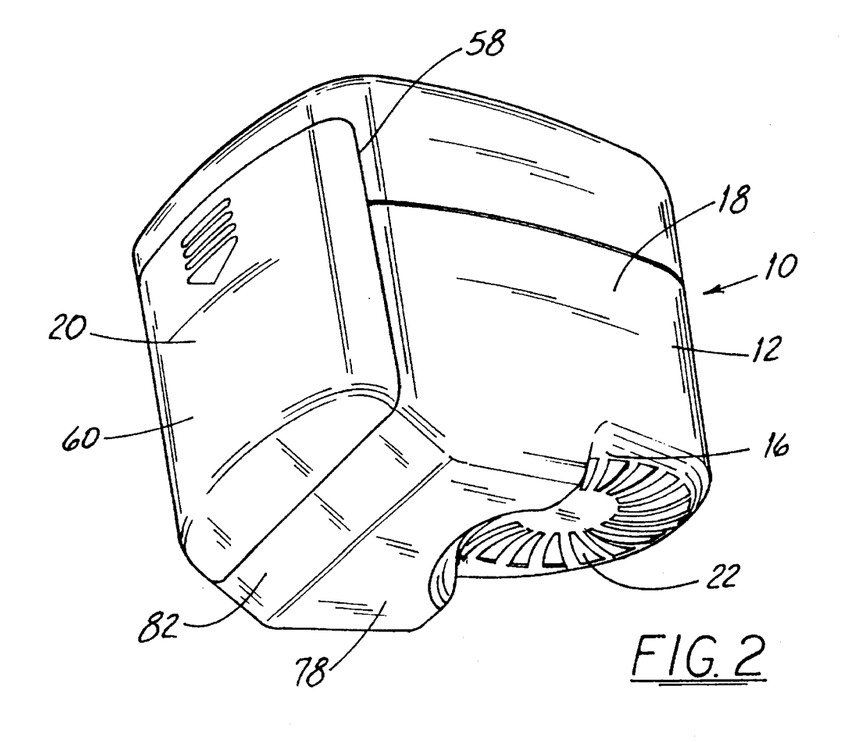
FIG. 2 is a front perspective view from beneath of the dispensing device of FIG. 1.

Turning now to the drawings, wherein like parts are indicated by like reference numbers, a first and preferred embodiment of the dispensing device of the invention for dispensing a volatile active ingredient into the air is shown generally at 10 in FIG. 1 and FIG. 2. The dispensing device 10 is intended for use with a refill assembly, described below, that has an air-transmitting substrate that bears the volatile active ingredient to be dispensed. The dispensing device 10 has an enclosed housing 12 having a modified box-like shape, with a roof 14, a floor 16, and sides 18. The front of the housing defines a housing face 20.

The housing 12 includes an intake vent 22 and an exit vent 24. The exit vent 24 is located in the housing roof 14, and the intake vent 22 preferably is located in the housing floor 16 or, in any event, in a location not obstructed by a table top or other flat surface upon which the dispensing device 10 may be supported. Internal surfaces of the housing 12 define an airflow path 26 that extends between the intake and exit vents.

Figure 8:
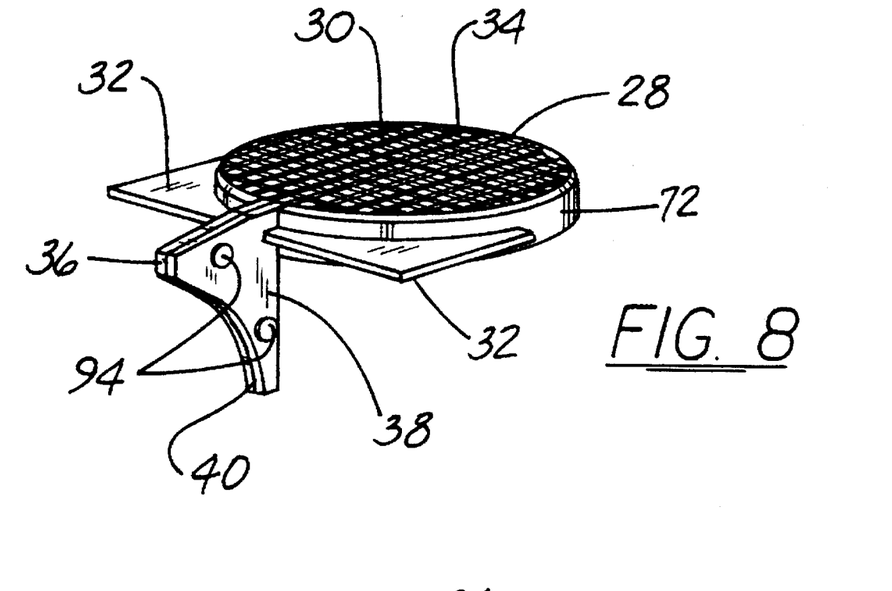
FIG. 8 is a mar perspective view from above of a refill assembly of the invention for use with the dispensing device of FIG. 1.
Figure 9:
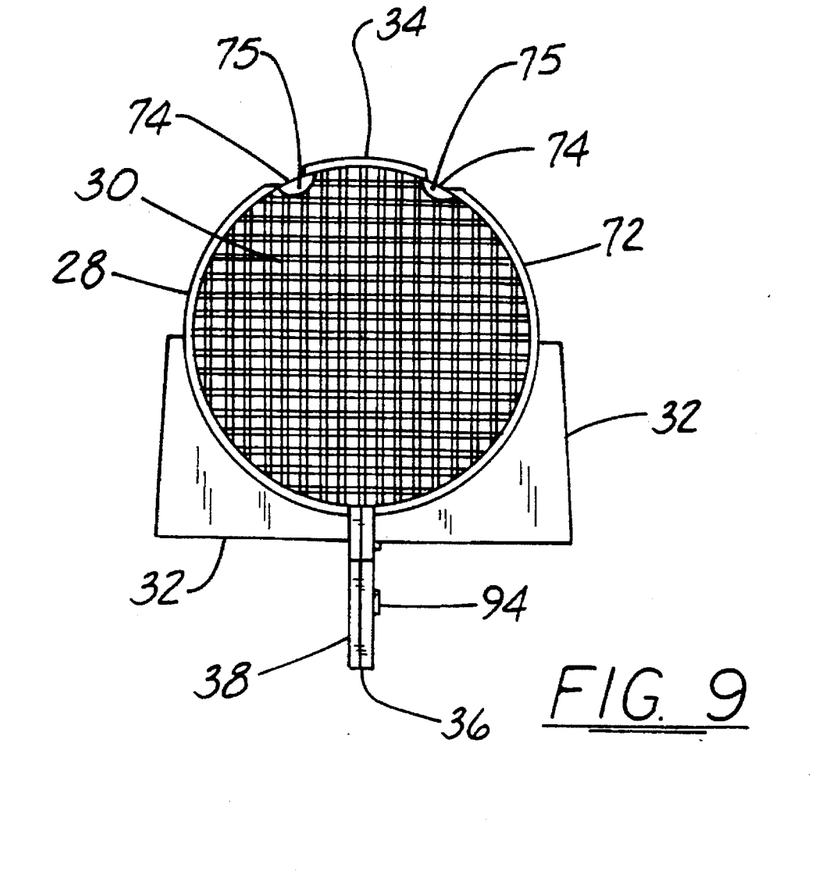
FIG. 9 is a top plan view of the refill assembly of FIG. 8.

The dispensing device 10 is intended for use with a refill assembly, a preferred embodiment of which is shown generally at 28 in FIGS. 8 and 9. The refill assembly 28 includes a substrate 30 preferred to be substantially planar and of a selected thickness determined by such factors as the bulk of substrate necessary to hold the amount of active ingredient desired. The substrate 30 is adapted to transmit an airflow through the substrate in a direction approximately normal to the plane of the substrate.

The substrate 30 is designed to be so placed in the airflow path 26 that air passing from the intake vent 22 to the exit vent 24 will of necessity pass through all or at least a part of the substrate. It is preferred that the shape and size of the substrate 30 be approximately the same as the cross-sectional size and shape of the airflow path 26 at the point that the substrate is to be held within the airflow path. Such an arrangement provides the most efficient use both of the air that flows through the airflow path 26 and the substrate 30. However, smaller or larger substrates are possible, as are substrates of different shapes. All such alternative embodiments are within the scope and spirit of the invention. In the preferred embodiment of the refill assembly shown at 28, the substrate 30 is a disk of a size sufficient to span and fill substantially the entire cross-sectional dimension of the airflow path 26 of the dispensing device 10, which, in the embodiment of the dispensing device shown at 10, is round at the point where the substrate is held in the airflow path.

The refill assembly 28 has at least one wing 32 to provide a surface of the refill assembly that can be used to guide insertion of the refill assembly into the dispensing device 10 and to support it when it is in place. The refill assembly 28 has a front 34 and rear 36. Preferably, the wing 32 extends rearwardly from the substrate 30 and is generally co-planar with the substrate. Also preferably, the wing 32 narrows slightly toward its front end to facilitate insertion of the refill assembly 28 into the dispensing device 10.

The refill assembly 28 includes a tab 38 that extends downwardly and rearwardly from the rear margin of the substrate 30, at a right angle to the substrate. The tab 38 provides a convenient structure for a user's fingertips to grasp while inserting or removing the refill assembly 28 from the dispensing device 10. The tab 38 has a brace surface 40 facing generally away from the substrate 30 and shaped to engage the surface of a battery under circumstances to be described, below. Preferably, the brace surface 40 is adapted to engage the curved surface of a cylindrical battery. Although this end could be achieved by allowing for brace surface 40 contact with the battery at selected points, the preferred shape of the brace surface is concave and semi-circular.

Other features of the refill assembly 28, together with the manner of its use, will be described, below.

The dispensing device 10 includes fan means for propelling air entering the housing 12 by way of the intake vent 22 along the airflow path 26, to pass through the substrate 30 and exit by way of the exit vent 24. Such fan means preferably is a battery powered fan, such as that shown schematically at 42 in FIGS. 3–6. In the preferred embodiment, the fan 42 is a modular unit in which the fan itself includes fan blades 44, seen in FIG. 5, and a fan motor 46, shown schematically in FIG. 5.

In the preferred embodiment shown in the drawings, the fan motor 46 is mounted within a fan housing 48, which is so oriented that air is propelled upwardly through the housing 12 of the dispensing device 10, to be discharged from the exit vent 24. Interior surfaces of the fan housing 48 are continuous with and substantially form a part of the airflow path 26. Preferably, the fan housing 48 is circular in horizontal cross-section to match the disk shape of the substrate 30. The fan blades 44 shown in the drawings are of the pinwheel or turbine sort and are preferred. However, a squirrel cage fan or any other fan means for propelling air along the airflow path are within the scope and spirit of the invention.

Figure 3:
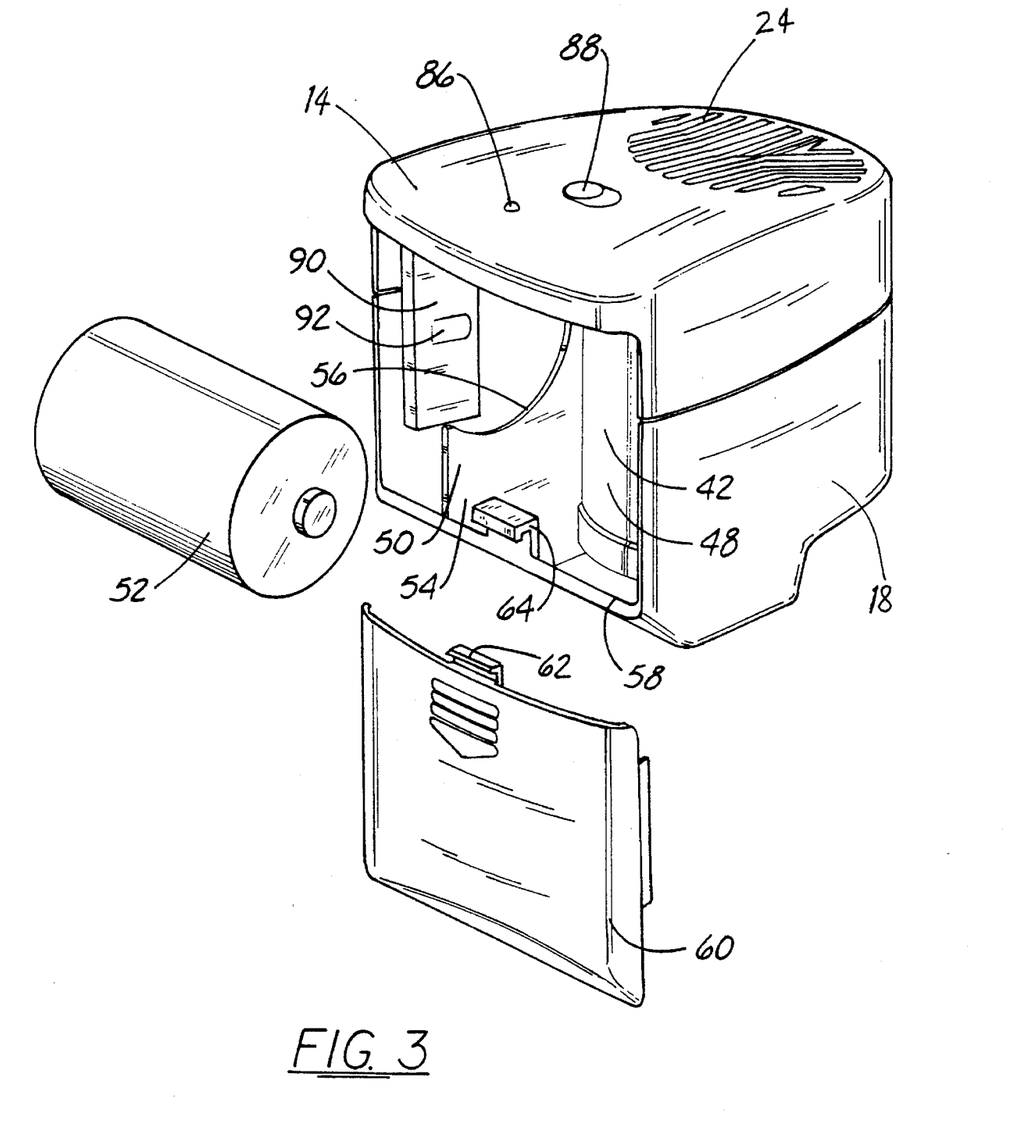
FIG. 3 is a front perspective view from above of the dispensing device of FIG. 1 with the door removed and a battery shown in the position appropriate for insertion into the device.
Figure 4:
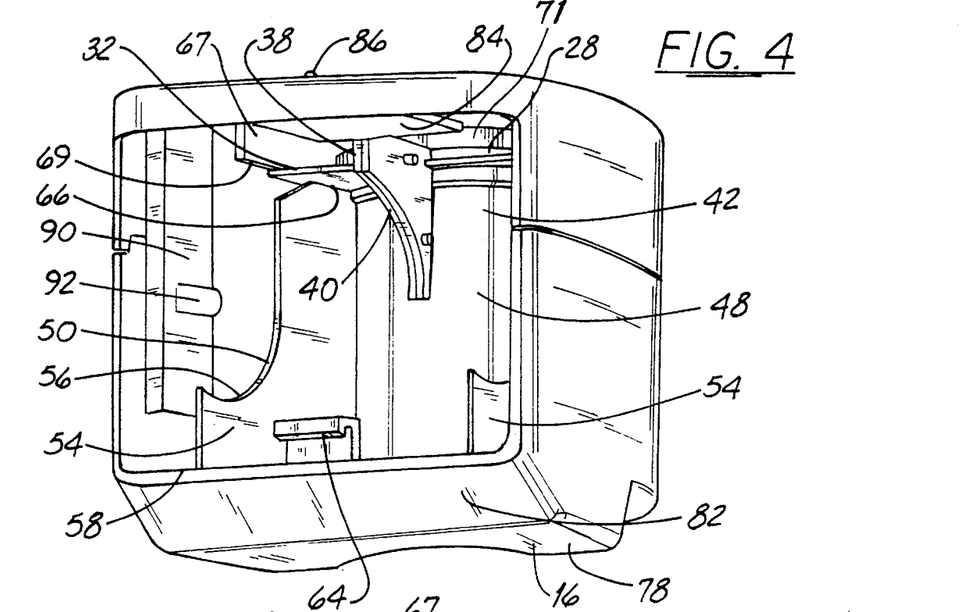
FIG. 4 is a from perspective view of the dispensing device of FIG. 1, from beneath, looking into the open door of the device.
Figure 7:
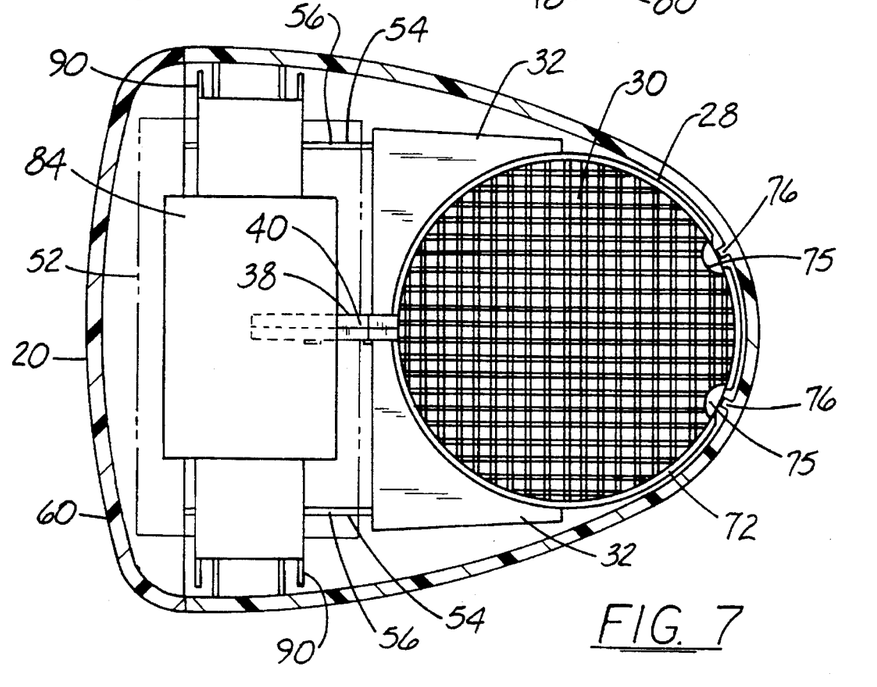
FIG. 7 is a cross-sectional view of the dispensing device of FIG. 1 taken along section line 7—7 of FIG. 1.

The dispensing device 10 also includes a battery holder 50 for a fan battery, such as the preferred, conventional D-cell battery shown at 52 in FIG. 3. The battery 52 is indicated in phantom in FIGS. 5 and 7. The dispensing device 10 includes refill assembly support means for removably supporting the refill assembly 28 with the substrate 30 located within the airflow path 26. The battery holder 50 holds the battery 52 in such a manner that a refill assembly 28 not fully inserted within the refill assembly support means blocks the placement of a battery in the battery holder, providing a signal to a user that the position of the refill assembly needs to be corrected.

In the preferred embodiment, two support members 54 extend upwardly from the floor 16 of the housing 12, each support member extending fore and aft within the housing, with one on each side of the fan 42. The support members 54 each have upwardly presented battery support surfaces 56 adapted to support the battery 52. Preferably, the support surfaces 56 are curved surfaces of a size selected to match the curved side of a conventional, cylindrical, D-cell battery, such as the battery shown at 52, although other particular geometries are possible and are within the scope and breadth of the invention.

The face 20 of the housing 12 has an access opening 58 through which the battery 52 may be inserted or retrieved. A door 60 closes the access opening 58. Preferably the door 60 slides upwardly from below in grooves (not shown) designed to engage the door. A door latch 62 located at the top margin of the door 60 and access opening 58 is formed of cooperating parts of the door and the housing 12 that snap together to retain the door in its closed position. The door is further secured by cooperating structures at the bottom margin of the door 60 and the bottom edge of the access opening 58, the cooperating structures joining to form a door hook 64. These structures are most easily understood from the cross-sectional view of FIG. 5.

When a cylindrical battery 52 is in place on the battery support surfaces 56, the battery support surfaces curve circumferentially under the side of the battery and forwardly sufficiently far to cradle the battery, so retaining a battery placed upon the support surfaces that it is not free to roll forward unless the door 60 is removed and the dispensing device 10 is tipped toward its face 20 to deliberately dump the battery out the access opening 58.

In the preferred embodiment, the refill assembly support means includes upwardly presented refill assembly support surfaces 66 formed in the support members 54. The refill assembly support means further includes retaining blades 67 extending downwardly from the roof 14, with one such retaining blade being located directly above each refill assembly support surface 66. Downwardly presented retaining surfaces 69 of the retaining blades 67 oppose the refill assembly support surfaces 66 to define a refill guide channel 70 therebetween. The refill guide channel 70 accepts in removable, sliding relation the wing 32 of the refill assembly 28. A user may insert a refill assembly 28 into the dispensing device 10 through the access opening 58. When fully inserted into the refill guide channel 70, the substrate 30 is properly located in the airflow path 26, with the wings 32 resting upon the refill assembly support surfaces 66 and retained beneath the retaining surfaces 69. When the user of the dispensing device 10 desires to change a spent refill assembly 28, the user may open the door 60, remove the battery 52, grasp the tab 38 of the refill assembly in the dispensing device, and draw out the spent refill assembly.

When properly located in the airflow path 26, the substrate 30 preferably is located immediately above the fan housing 48. Preferably, in the space between the roof 14 and a substrate 30 so located, the rearward portions of the airflow path 26 are defined by a semi-circular collar 71 that directs air that has passed upwardly through the substrate 30 to the exit vent 24.

Figure 5:
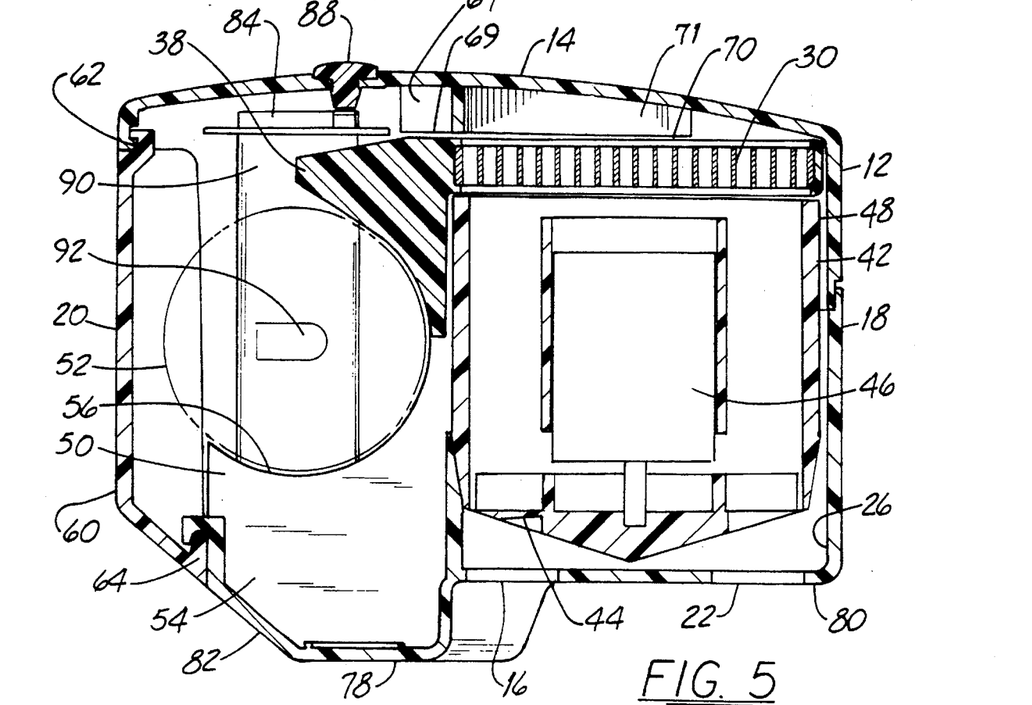
FIG. 5 is a cross-sectional view of the dispensing device of FIG. 1 taken along section line 5—5 of FIG. 1.
Figure 6:
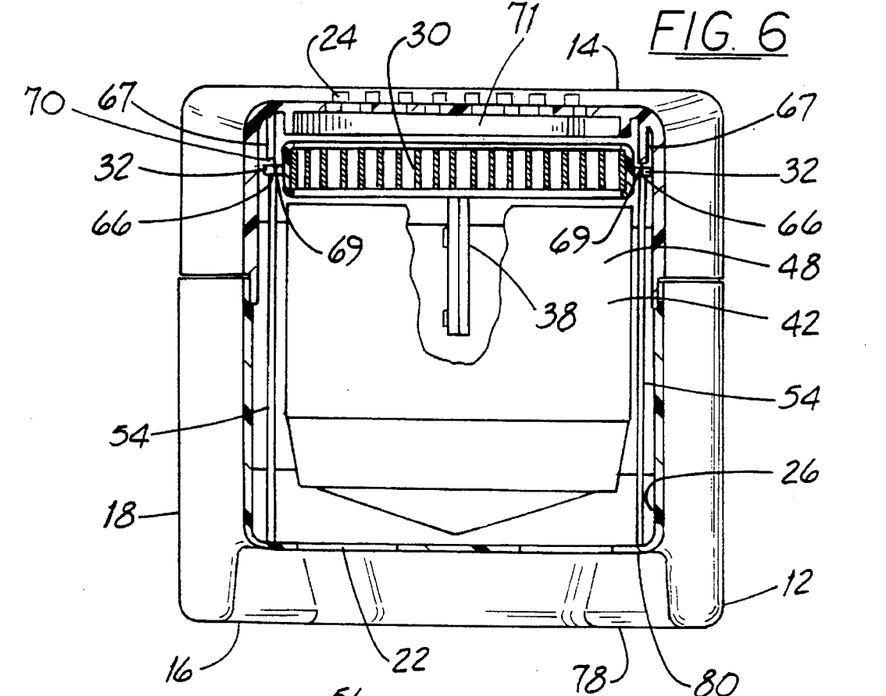
FIG. 6 is a cross-sectional view of the dispensing device of FIG. 1 taken along section line 6—6 of FIG. 1.

As can be best appreciated in the cross-sectional view of FIG. 5, the dimensions of the refill assembly 28 are selected to be such that, unless the refill assembly is properly thrust forward so that the substrate 30 entirely fills the airflow path 26, the brace surface 40 of the tab 38 projects into the space to be occupied by the battery 52, blocking its insertion into the battery holder 50, as has been mentioned, above. However, when the refill assembly 28 is correctly inserted within the refill guide channel 70, the curve of the brace surface 40 substantially forms a continuation of the curve of the battery support surfaces 56, allowing the battery 52 to be easily put into place.

When the battery 52 is properly located on the battery support surfaces 56 of the battery holder 50, contact between the curved side of the cylindrical battery and the brace surface 40 serves to retain the refill assembly 28 in proper position. Thus, the presence of a battery 52 correctly held in the battery holder 50 blocks the removal from the airflow path 26 of a refill assembly 28 supported in the airflow path by the refill assembly support means. By this means, successful placement of a battery 52 in the battery holder 50 serves to both verify and maintain the correct placement of the refill assembly 28 in the airflow path 26. Although the cylindrical D-cell shown in the drawings, with the corresponding shape of brace surface 40 shown, is preferred as an effective and convenient shape, the same basic arrangement may be accomplished with batteries and brace surfaces of other shapes. Such alternative arrangements are within the breadth and scope of the invention.

The battery holder 50 as described and shown is adapted to hold a cylindrical battery 52 adjacent to the airflow path 26, with the battery's longitudinal axis oriented approximately at a right angle to the direction of airflow within the airflow path. So held, the battery 52 in no way impinges upon or obstructs the airflow path. This positioning of the battery 52, together with the interactive and cooperating surfaces of the refill assembly tab 38 and battery support surfaces 56, serves both to create a compact and convenient design and also to allow the battery to be used both as a power source and as a device to hold the refill assembly 28 in place. In turn, the refill assembly 28 not only is adapted to hold the substrate 30 within the airflow path 26 but also serves to so interact with the battery 52 as to verify the successful and correct placement of those structures that must be periodically removed and replaced by a user of the dispensing device.

In the embodiment shown at 28, the refill assembly includes a retainer band 72 that extends around the circumference of the substrate 30 to secure it to the rest of the refill assembly. The retainer band 72 preferably includes band gaps 74, which are interruptions in the edgewardly facing surface of the retainer band. The retainer band 72 is held together at the band gaps by gap bridges 75 that extend generally parallel to the plane of the substrate 30. Locator ridges 76 are formed within the housing that matingly engage the band gaps 74 when the refill assembly 28 is in proper position, with the substrate 30 in the airflow path 26. The cooperating band gaps 74 and locator ridges 76 serve to reduce sideways movement of the substrate 30.

Figure 10:
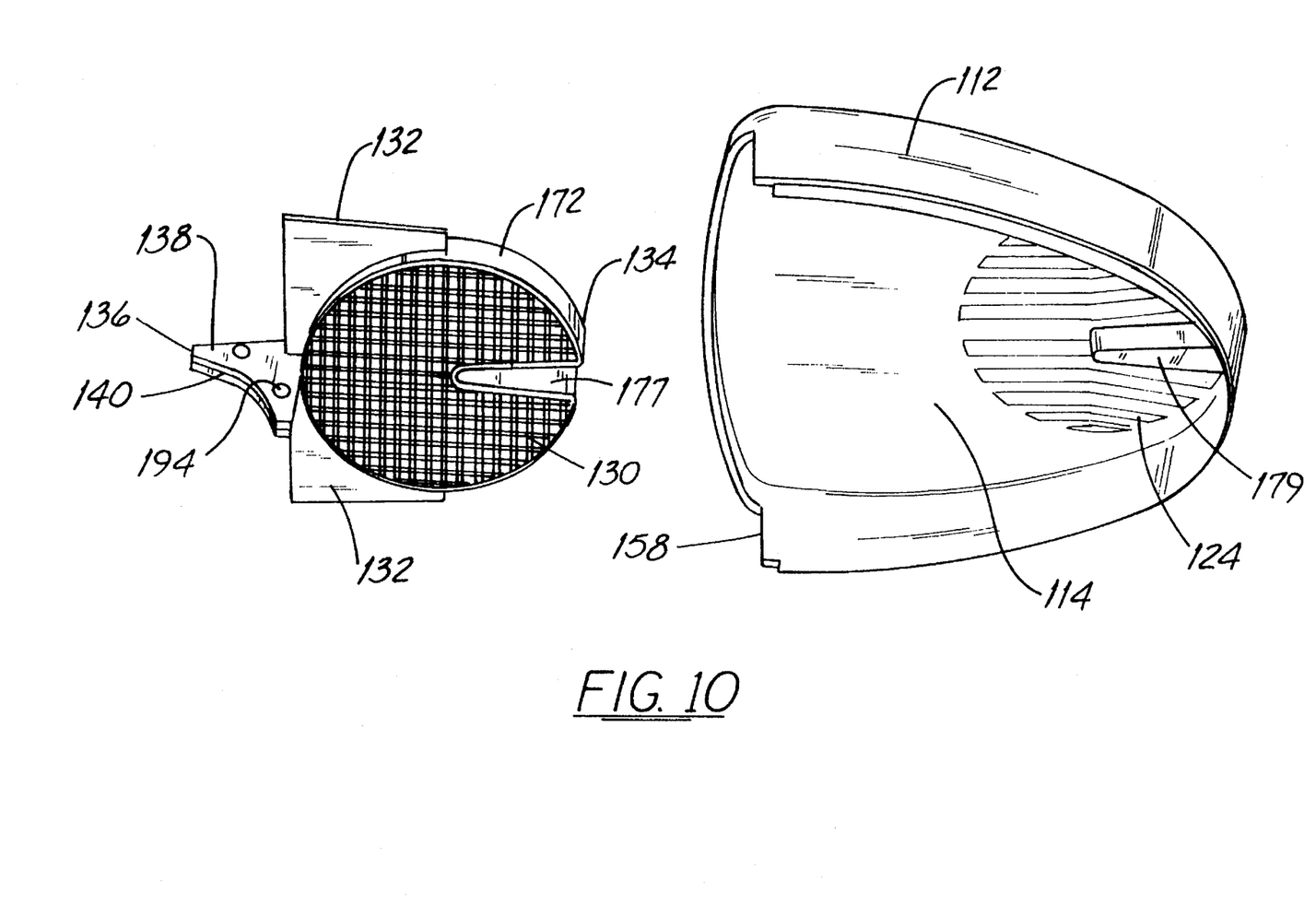
FIG. 10 is a side perspective view from beneath of an alternative embodiment of the refill assembly of FIG. 8, shown in exploded relation with respect to an alternative embodiment of the upper housing section of the dispensing device of FIG. 1.

An alternative embodiment of the refill assembly is shown generally at 128 in FIG. 10. Features of the embodiment of the refill assembly shown at 128 that correspond to features of the embodiment shown at 28 and discussed above are given corresponding reference numbers, increased by 100. The substrate 130 when held within the retainer band 172 is substantially rigid. The embodiment shown at 128 includes a locator notch 177 that extends inwardly from the forward margin of the substrate 130 at a location remote from the tab 138 and is open toward the margin.

The refill assembly 128 is adapted to be used with a modified embodiment of the dispensing device 10, a portion of the housing of which is shown in FIG. 10, with parts corresponding to the embodiment shown at 10 given corresponding reference numbers increased by 100. A locator rib 179 extends forwardly from the wall of the housing 112 opposite to the access opening 158 and downwardly from the roof 114. The locator rib 179 is adapted to be engaged by the locator notch 177 to aid in reliably orienting and securing the substrate 130 within the airflow path. The locator notch 179 functionally generally corresponds to the band gaps 74 of the embodiment of the refill assembly shown in 28 in FIGS. 8 and 9.

Preferably the substrate 30 is a substantially flat coil of corrugated cardboard with the corrugation channels thereof oriented substantially parallel to the longitudinal axis of the coil. Alternatively, the substrate may be composed of a substantially flat, finely divided, channeled or honeycombed structure molded of plastic. The latter material is especially useful if a locator notch 177 is desired that extends into the substrate 130 for a considerable distance in that such structures may be molded with relative ease but are more difficult to manufacture as a non-molded structure.

The dispensing device 10 is intended to be supported by a generally flat surface such as a table top. The housing floor 16 includes a generally planar foot 78 upon which the housing 12 may rest when placed on such a surface. Preferably the floor 16 of the housing 12 also includes a downwardly facing, cantilevered overhang 80 that is elevated above the level of the foot 78 so as to be spaced above the supporting surface when the foot is resting thereupon. The intake vent 22 may then be conveniently formed in the cantilever overhang, providing an unobstructed route for air to flow in through the intake vent. The air flow path 26 may then be an essentially straight, vertical path upwardly from the intake vent 22 to the exit vent 24 located in the roof 14 of the housing 12.

It is desirable that a user may orient the dispensing device 10 in alternative positions to allow the air flow exiting the exit vent 24 to be directed either upwardly or forwardly, at an angle. Such an arrangement allows the dispensing device 10 to be placed either in the middle of a room, with the air flow directed upwardly, or at the side of a room or otherwise to one side of an area to be exposed to the air flow expelled through the exit vent 24. To accomplish this end, the floor 16 includes an angled support surface 82 that extends upwardly from the forward margin of the foot 78 to the face 20 of the housing 12, at an acute angle to the plane of the foot.

The battery holder 50 positions the battery 52 forward within the housing 12. The weight of the battery 52 so interacts with the weights of the components of the dispensing device 10 that the center of gravity of the dispensing device and battery combination is above the foot 78, when the foot is resting on a horizontal surface, and also is above the angled support surface 82 when the angled support surface is resting on the horizontal surface. By this means, the dispensing device 10 may be supported alternatively and with positional stability on either the foot 78 or the angled support surface 82. Bracing or other means to preserve the position of the housing 12 on a supporting surface is not required. By choosing between use of the foot 78 and angled support surface 82, a user may direct the airflow either straight up or upward and to the front of the dispensing device 10. Furthermore, the battery holder 50 may be designed to so position the battery 52 that the center of gravity of the dispensing device 10 is also above the face 20, when the face is resting on a horizontal surface. This arrangement allows the dispensing device 10 to be supported alternatively and with positional stability by either the foot 78, the angled support surface 82, or the face 20 to direct the airflow exiting the exit vent 24 either upwardly, upwardly at a forward angle, or horizontally forward.

Conventional batteries such as the D-cell shown at 52 have a limited useful capacity. Similarly, the substrate 30 of a refill assembly 28 also can bear only a finite quantity of volatile active ingredient, and, preferably, the volatile active ingredient is applied to the substrate 30 in a controlled amount. That amount is selected to be depleted approximately upon the passage through the air flow path 26 of that volume of air that the fan means will deliver before an initially fresh battery is discharged below a selected level. Thus, depletion of the battery 52 will correspond with active ingredient depletion and will signal the need to replace both the battery and the refill assembly 28.

Preferably the dispensing device 10 of the invention includes a control circuit, shown schematically in the drawings at 84. The control circuit 84 is adapted to sense the condition of the battery 52, preferably by responding to voltage drop. The control circuit 84 turns off the power to the fan means when the battery condition reaches the level that should correspond to or just anticipate active ingredient depletion, at least to the point where replacement of the refill assembly 28 is desirable. It is preferred that the control circuit include signal means to signal the depletion of the battery 52 to a selected level approaching that at which power to the fan means will be turned off. Consequently, a user of the dispensing device 10 is given advance warning of device shut down. The user may then replace the battery 52 and refill assembly 28 and thus avoid an interruption of service from the dispensing device 10.

When the control circuit 84 is located adjacent to the roof 14, as is shown in the drawings, the signal means may conveniently be an LED or comparable small signal light such as that shown at 86, projecting from the roof 14. A switch 88 may also be conveniently located in the roof 14 to interact with a switch mechanism (not shown) manufactured as a part of the control circuit 84. Preferably the control circuit 84 is located above the battery holder 50, and electrical conduits 90 extend from the control circuit down opposite sides 18 of the housing 12. The electrical conduits 90 have spring contacts 92 formed therein, inwardly biased to contact the ends of a battery 52 held in the battery holder 50. Although the physical arrangement just described is convenient, clearly other means for conveying electrical power from the battery 52 to the fan means are possible and are within the breadth and scope of the invention.

Both the dispensing device 10 and the refill assembly of the invention may be conveniently manufactured by conventional injection molding techniques. If the substrate 30 is not unitarily molded with the rest of the refill assembly 28, the retainer band 72 and tab 38 may be split so that the refill assembly may first be molded as an open structure, separate from the substrate, hinged at the forward extreme of the retainer band (hinge not shown in the drawings). This open structure may then be closed at its hinge and assembled around the substrate 30. The two split halves of the tab 38 may be joined with heat-deformed rivets, such as those visible at 94 in FIGS. 8–10.

INDUSTRIAL APPLICABILITY

The effective dispensing of volatile active ingredients into the air is industrially applicable to insect control, as well as to air treatment for odors and other purposes. Especially when intended for use by consumers, dispensing devices that provide for a more inevitable correct placement and retention of refill assemblies, alternative device orientations, and means to signal a user when the battery and active ingredient are depleted all increase the practicality and applied usefulness of such devices.

While preferred forms of the invention have been shown in the drawings and have been described, variations in the preferred forms apparent to those skilled in the art will be within the scope and breadth of the invention. Consequently, the invention should not be construed as limited to the specific preferred embodiments shown and described but, instead, should be understood in terms of the following claims.

We claim:

1. A dispensing device for dispensing a volatile active ingredient from an air-transmitting substrate that forms a part of a refill assembly, the dispensing device comprising
   a. a housing with an intake vent and an exit vent, internal surfaces of the housing defining an airflow path extending between the intake and exit vents;
   b. refill assembly support means for removably supporting the refill assembly with the substrate located in the airflow path;
   c. battery-powered fan means for propelling air entering the housing by way of the intake vent along the airflow path, to pass through the substrate and exit by way of the exit vent; and
   d. a battery holder for holding a battery for powering the fan means in such a manner that a refill assembly not fully inserted within the refill assembly support means blocks the placement of a battery in the battery holder, and the presence of a battery correctly held in the battery holder blocks the removal from the airflow path of a refill assembly supported in the airflow path by the refill assembly support means;

whereby successful placement of a battery in the battery holder serves to both verify and maintain the correct placement of the refill assembly in the airflow path.

2. The dispensing device of claim 1 wherein the housing includes a housing roof, sides, and floor, the housing floor including
   a. a foot upon which the housing may rest when placed on a supporting, generally flat surface; and
   b. a downwardly facing, cantilevered overhang elevated above the level of the foot so as to be spaced above the supporting surface when the housing foot is resting thereon;

and wherein the intake vent is formed in the cantilevered overhang and the exit vent is formed in the housing roof.

3. The dispensing device of claim 1 wherein
   a. the housing includes a housing face at the front of the housing, together with a housing roof, sides, and floor, the housing floor including a foot upon which the housing may rest when placed on a supporting, generally flat surface and an angled support surface extending upwardly to the face from the forward margin of the foot at a selected angle to the foot;
   b. the exit vent is located in the housing roof to vent the airflow upwardly when the housing is resting on the foot; and
   c. the battery holder positions the battery sufficiently far forward within the housing that the weight of the battery so interacts with the weights of the components of the dispensing device that the center of gravity of the dispensing device is above the foot, when the foot is resting on a horizontal surface, and is above the angled support surface, when the angled support surface is resting on a horizontal surface, to allow the dispensing device to be supported alternatively and with positional stability by either the foot or the angled support surface to direct the airflow exiting the exit vent either upwardly or upwardly at a forward angle.

4. The dispensing device of claim 1 wherein:
   a. the battery holder is adapted to hold a cylindrical battery adjacent to the airflow path, with the battery's longitudinal axis oriented at substantially a right angle to the direction of airflow within the airflow path; and
   b. the refill assembly support means is adapted to hold a refill assembly that has a front and a rear and includes an air-transmitting substrate to be held in the airflow path and a tab attached to the rearward margin of the substrate, the tab having a brace surface that faces generally away from the substrate and is concavely curved to match the curved side of the cylindrical battery, the refill assembly support means being adapted to so hold the refill assembly that the brace surface lies against the battery when the battery is held within the battery holder and the refill assembly is correctly positioned within the refill assembly support means, with the substrate held within the airflow path.

5. The dispensing device of claim 4 adapted for use with a refill assembly whose substrate has a locator notch that extends inwardly from a location on the margin of the substrate remote from the tab and is open toward the margin, wherein the refill assembly support means includes a locator rib adapted to enter and engage the locator notch to aid in reliably orienting and securing the substrate within the airflow.

6. The dispensing device of claim 4 wherein the refill assembly support means includes refill assembly support surfaces adapted to receive in cooperating, sliding relation wings extending sidewardly and rearwardly from the substrate of the refill assembly to guide and properly orient the insertion of the refill assembly into the refill assembly support means.

7. The dispensing device of claim 1 adapted for use with a battery of limited useful capacity and a refill assembly bearing a volatile active ingredient in a finite amount selected to be depleted approximately upon the passage through the airflow path of that volume of air which the fan means will deliver before an initially fresh battery is discharged below a selected level, the dispensing device including a control circuit adapted to sense the condition of the battery and to interrupt the power to the fan means when the battery is depleted to a level selected to be such that the active ingredient on the substrate may be expected to have been depleted to the point where replacement of the refill assembly is desirable.

8. The dispensing device of claim 7 wherein the control circuit includes signal means to signal the depletion of the battery to a selected level approaching that level at which power to the fan means will be interrupted, whereby a user of the dispensing device may have advance warning to be prepared to replace the battery and refill assembly and avoid an interruption of service from the dispensing device.

9. An air-transmitting refill assembly for use with the dispensing device for dispensing a volatile active ingredient of claim 1, the refill assembly having a front and a rear and comprising an air-transmitting substrate and a tab attached to the rearward margin of the substrate, the tab having a brace surface facing generally away from the substrate and shaped to engage the surface of a battery being held within the battery holder of the dispensing device for dispensing a volatile active ingredient.

10. The refill assembly of claim 9, wherein the brace surface is concave and adapted to engage the curved surface of a cylindrical battery being held by the dispensing device adjacent to the airflow path, with the battery's longitudinal axis oriented at substantially a right angle to the direction of airflow within the airflow path.

11. The refill assembly of claim 9, wherein the substrate has a locator notch that extends inwardly from a location on the margin of the substrate remote from the tab and is open toward the margin to engage a corresponding locator rib extending from the housing of the dispensing device for dispensing a volatile active ingredient to aid in reliably orienting and securing the substrate within the airflow of the dispensing device.

12. The refill assembly of claim 9, wherein the air-transmitting substrate is substantially flat and at least one guide wing extends from the substrate with an orientation generally co-planar thereto to aid in guiding and properly orienting the insertion of the refill assembly into the refill assembly support means of the dispensing device when the refill assembly support means thereof includes refill assembly support surfaces.

13. The refill assembly of claim 9 wherein the air-transmitting substrate is a round coil of corrugated cardboard with the corrugation channels thereof oriented substantially parallel to the longitudinal axis of the coil.

14. The refill assembly of claim 9 wherein the air-transmitting substrate is a finely divided, channeled, or honeycombed structure molded of plastic.

15. A dispensing device for dispensing a volatile active ingredient from an air-transmitting substrate that forms a part of a refill assembly, the dispensing device comprising a. a housing including a housing face forming the front of the housing, together with a housing roof, sides, and floor, the housing floor including a foot upon which the housing may rest when placed on a supporting, generally flat surface and an angled support surface extending upwardly to the face from the forward margin of the foot at a selected angle to the foot, the housing having an intake vent and an exit vent, internal surfaces of the housing defining an airflow path extending between the intake and exit vents, the exit vent being located in the housing roof to vent the airflow upwardly when the housing is resting on the foot;
   b. refill assembly support means for supporting the refill assembly with the substrate in the airflow path;
   c. battery-powered fan means for propelling air entering the housing by way of the intake vent along the airflow path, to pass through the substrate and exit by way of the exit vent; and
   d. a battery holder to hold within the housing a battery to power the fan means, with the battery positioned sufficiently far forward that the weight of the battery so interacts with the weights of the components of the dispensing device that the center of gravity of the dispensing device is above the foot, when the foot is resting on a horizontal surface, and is above the angled support surface, when the angled support surface is resting on a horizontal surface, to allow the dispensing device to be supported alternatively and with positional stability by either the foot or the angled support surface to direct the airflow exiting the exit vent either upwardly or upwardly at a forward angle.

16. The dispensing device of claim 15 wherein the housing floor includes a downwardly facing, cantilevered overhang elevated above the level of the foot so as to be spaced above the supporting surface when the housing foot is resting thereon, and wherein the intake vent is formed in the cantilevered overhang.

17. The dispensing device of claim 15 wherein the battery holder so positions the battery that the center of gravity of the dispensing device is also above the face, when the face is resting on a horizontal surface to allow the dispensing device to be supported alternatively and with positional stability by either the foot, the angled support surface, or the face to direct the airflow exiting the exit vent either upwardly, upwardly at a forward angle, or horizontally forward.

18. The dispensing device of claim 15 adapted for use with a battery of limited useful capacity and a replaceable refill assembly whose substrate bears a finite amount of volatile active ingredient selected to be such that it will be depleted approximately upon the passage through the airflow path of the volume of air that the fan will deliver before an initially fresh battery is discharged below a selected level, the dispensing device including a control circuit adapted to sense the condition of the battery and turn off the power to the fan means when the battery is depleted to a level selected to be such that the active ingredient may be expected to have been depleted to the point where replacement of the refill assembly is desirable.

19. The dispensing device of claim 18 wherein the control circuit includes signal means to signal the depletion of the battery to a selected level approaching that level at which power to the fan means will be turned off, whereby a user of the dispensing device may have advance warning to be prepared to replace the battery and refill assembly and avoid an interruption of service from the dispensing device.

20. The dispensing device of claim 15 wherein a. the refill assembly support means is adapted to removably support the refill assembly, and
   b. the battery holder is adapted to hold a battery adjacent to the airflow path in such a manner that a refill assembly not fully inserted within the refill assembly support means blocks the placement of a battery in the battery holder, and the presence of a battery correctly held in the battery holder blocks the removal from the airflow path of a refill assembly supported in the airflow path by the refill assembly support means;

whereby successful placement of a battery in the battery holder serves to both verify and maintain the correct placement of the refill assembly in the airflow path.

21. The dispensing device of claim 20 wherein:

a. the battery holder is adapted to hold a cylindrical battery, with the battery's longitudinal axis oriented at a right angle to the direction of airflow within the airflow path; and
   b. the refill assembly support means is adapted to hold a refill assembly that has a front and a rear and includes an air-transmitting substrate adapted to be held in the airflow path and a tab attached to the rearward margin of the substrate, the tab having a brace surface facing generally away from the substrate and concavely curved to match the curved side of the cylindrical battery, the refill assembly support means being adapted to so hold the refill assembly that the brace surface lies against the battery when the battery is held within the battery holder and the refill assembly is correctly positioned within the refill assembly support means, with the substrate held within the airflow path.

22. The dispensing device of claim 21 adapted for use with a refill assembly whose substrate has a locator notch that extends inwardly from a location on the margin of the substrate remote from the tab and is open toward the margin, wherein the refill assembly support means includes a locator rib adapted to enter and engage the locator notch to aid in reliably orienting and securing the substrate within the airflow.

* * * * *